United States Patent
Nordgren et al.

(10) Patent No.: US 6,599,249 B1
(45) Date of Patent: Jul. 29, 2003

(54) INTRAOPERATIVE ULTRASOUND PROBE WITH AN INTEGRATED ACOUSTIC STANDOFF

(75) Inventors: Timothy Nordgren, Bothell, WA (US); James Jago, Seattle, WA (US); Gregory J. Friend, Seattle, WA (US); Douglas Maxwell, Woodinville, WA (US); Scott Easterbrook, Seattle, WA (US); Deborah Imling, North Bend, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/076,766

(22) Filed: Feb. 14, 2002

(51) Int. Cl.[7] .................................................. A61B 8/14
(52) U.S. Cl. ..................................................... 600/459
(58) Field of Search ................................ 600/407–471; 367/7, 11, 130, 138; 310/320–334; 29/25.35; 128/916; 601/2–4

(56) References Cited

U.S. PATENT DOCUMENTS

| | | | | |
|---|---|---|---|---|
| 5,033,456 A | * | 7/1991 | Pell et al. | 601/4 |
| 5,127,410 A | * | 7/1992 | King et al. | 600/459 |
| 5,505,205 A | * | 4/1996 | Solomon et al. | 600/459 |
| 6,159,149 A | * | 12/2000 | Erikson et al. | 600/437 |

* cited by examiner

Primary Examiner—Marvin M. Lateef
Assistant Examiner—Ali M. Imam
(74) Attorney, Agent, or Firm—Edward A. Uhl

(57) ABSTRACT

An ultrasound probe is provided for imaging and diagnosing areas of interest that are in immediate contact with the probe. The probe provides an integrated standoff comprised of a rubber material having optimal acoustic characteristics. The lens is directly applied to the transducer and the standoff is applied to the lens such that the focal zone is placed at the area immediately below the patient contact surface of the probe. The lens material also encapsulates the transducer and provides reliable protection against electrical shock. The standoff is also separated from the surface being examined by a cap comprised of a biocompatible elastomer having high chemical and abrasive resistance that enables the probe to be easily sterilized and disinfected and provides further protection against electrical shock. The use of a standoff with optimal acoustic properties in, combination with the arrangement of the lens, standoff and cap provides a probe with a focal zone placed at the area immediately below the probe. The lens, standoff and cap are spatially arranged to minimize the volume of the distal transducer section and overall probe such that the probe is easy to manipulate.

18 Claims, 5 Drawing Sheets

INTRAOPERATIVE ULTRASOUND PROBE WITH AN INTEGRATED ACOUSTIC STANDOFF

This invention relates to ultrasonic diagnostic imaging system probes, and in particular to an ultrasound probe having an integrated acoustic standoff that is suited for imaging and diagnosing organs of the body and arterial vessels during surgery.

Ultrasonic diagnostic imaging systems are in widespread use for performing ultrasonic imaging and measurements of the human body through the use of ultrasound probes. Ultrasound probes are generally used external to the body in non-invasive procedures but can also be used internal to the body being examined during surgical procedures. Ultrasound probes are used to view the internal structure of a body by creating a scan plane or volume, which is produced from an array of transducers. The transducers transmit pulses of acoustic energy or beams into the body and receive returning echoes of that energy as they are reflected from internal structures of the body. A correctly focused beam is achieved by using an acoustic lens. The focal zone is the range over which the beam is sufficiently narrow relative to the anatomical features in the area interest. Beyond the focal zone the beams begin to diverge and may become larger than the relevant anatomical features. These relative beam sizes determine the resolution of the ultrasound image.

In surgical procedures, such as vascular surgery, the ultrasound probe may be used to image and diagnose the interior of arteries, or the blood flow of a vessel or organ. In other surgical procedures, such as transplants, for example, the ultrasound probe may be used to verify successful attachment of renal arteries. Similarly, in non-invasive procedures such as musculoskeletal or peripheral vascular procedures, the ultrasound probe may be used to image or diagnose an area located near the surface of the skin. Such procedures require the ultrasound probe to have focal properties that enable it to produce a focused image of tissues and structures that are in immediate contact with the probe. Such focal properties include having a focal zone that is in immediate contact with the probe.

Lens and standoff materials have been used alone or in combination to attempt to provide a probe with such a focal zone. Lenses are used because the focal zone can be controlled by placing a lens in the path of the ultrasonic beam to cause the beam to focus or converge at a faster rate as the beam travels away from the transducer. If the beam passes through a convex lens having an acoustic velocity slower than the medium that it is being transmitted into, the beam will converge even faster and will place the focal zone at a shorter distance from the transducer. Standoffs are used between the transducer and the surface being examined to place the focal zone at a certain distance from the transducer. An optimal standoff or standoff-lens combination for the procedures described above would place the focal zone immediately below the area in immediate contact with the probe. As discussed below, there are many factors such as standoff material, standoff height and standoff-lens arrangements that affect the location of the focal zone.

An ultrasound probe that attempts to place the focal zone at the area in immediate contact with the probe is described in U.S. Pat. No. 5,381,795, the contents of which are incorporated herein by reference. That patent describes an ultrasound probe with an RTV rubber boot that encapsulates the transducer and also forms an external standoff and lens for providing a focal zone in the area near the surface contacting the probe. While the boot provides a standoff that can be easily cleaned, disinfected or sterilized, the arrangement of the standoff and lens in that patent does not provide an ultrasound probe that optimally places the focal zone at or immediately below the surface contacting the area of interest.

As the ultrasonic beams leave the transducer of that patent, the beams may slightly converge as they pass through the flat standoff. Since the convex lens is located at the patient contact surface of the probe the focusing effect of the lens itself does not begin until somewhere past the contact surface. Such an arrangement of the standoff and lens does not optimally locate the focal zone for imaging areas that are in immediate contact with the probe.

In addition to the arrangement of the standoff and lens, the choice of standoff material can also affect the location of the focal zone. In choosing a standoff material for a probe with a focal zone in the area in immediate contact with the probe, it is desirable to have a standoff with optimal acoustic characteristics (impedance, velocity and attenuation). In a standoff with optimal acoustic characteristics the impedance and velocity will closely match the characteristics of body tissue and the acoustic attenuation of the standoff will be minimized as much as possible. In reference to acoustic characteristics, an optimal and desired standoff material will have a longitudinal velocity between 1.4 to 1.6 mm/psec, an impedance between 1.4 MRayls and 1.60 MRayls, and an attenuation no greater than 0.10 dB/mm/MHz.

When the attenuation is minimized and the impedance and velocity characteristics of a standoff closely match body tissue, the quality of the ultrasound image is higher because the ultrasonic beams and returning echoes are not distorted, or reflected and are minimally attenuated as they pass through the standoff. Also, with optimal acoustic characteristics, the ultrasonic beams traveling through the standoff will be able to converge at a faster rate to form a focal zone located closer to the area in immediate contact with the probe, if desired.

In probes that require the standoff to come into contact with the surface being examined, the biocompatibility, and chemical and mechanical properties of the standoff material become more important. In such instances, the standoff material should be biocompatible, have strong chemical resistance and a strong mechanical or abrasive resistance, which makes the standoff easier to manipulate, increases the durability and usable life of the standoff, provides a material that can be easily cleaned, disinfected or sterilized, and provides a material that can act as an electrical insulator.

A problem arises when choosing a standoff material with strong chemical and mechanical properties because as such properties are optimized, the acoustic characteristics become less than optimal. For instance, a standoff material comprised of RTV rubber will have chemical and mechanical properties that make the standoff easier to manipulate, clean, disinfect or sterilized but such material will have less than optimal acoustic characteristics. That problem creates a conflict in standoff material choice where a focal zone is desired in the area in immediate contact with the probe and where the standoff material must have strong chemical and mechanical properties. In such cases a standoff with optimal acoustic properties is desired to increase image quality as explained above and to provide greater flexibility in choosing the thickness of the standoff for focal zone placement. As the chemical and mechanical properties are made stronger, the image quality is negatively affected and the maximum thickness of the standoff is limited, thus decreasing flexibility in placing the focal zone in the area in immediate contact with the probe.

Also, standoffs that come into contact with the surface being examined are generally disposable and must be replaced and stocked, and may require additional manipulation by the user of the probe, which distracts the user from the procedure at hand. It is important in surgical procedures that the size and shape of the probe permit the user of the probe to manipulate the probe with ease.

Accordingly, it is desirable to have an ultrasonic probe with a standoff integrated into the probe and strategically arranged with the lens for imaging and diagnosing areas of interest that are in immediate contact with the probe. The standoff materials of such a probe should have optimal acoustic properties with little or no regard for the chemical or mechanical properties such that the standoff may be thicker, if desired, to place the focal zone at the area in immediate contact with the probe. It is also desirable that the probe will provide reliable protection against electrical shock, may be properly sterilized and disinfected, and that the standoff can be used for the life of the probe. It is also desirable that the probe is easy to manipulate.

In accordance with the principles of the present invention, an ultrasound probe is provided for imaging and diagnosing areas of interest that are in immediate contact with the probe. The probe provides an integrated standoff comprised of a rubber material having optimal acoustic characteristics. The lens is directly applied to the transducer and the standoff is applied to the lens such that the focal zone is placed at the area immediately below the patient contact surface of the probe. The lens material also encapsulates the transducer and provides reliable protection against electrical shock. The standoff is also separated from the surface being examined by a cap comprised of a biocompatible elastomer having high chemical and abrasive resistance that enables the probe to be easily sterilized and disinfected and provides further protection against electrical shock. The use of a standoff with optimal acoustic properties in combination with the arrangement of the lens, standoff and cap provides a probe with a focal zone placed at the area immediately below the probe. The lens, standoff and cap are spatially arranged to minimize the volume of the distal transducer section and overall probe such that the probe is easy to manipulate.

Figure 1:
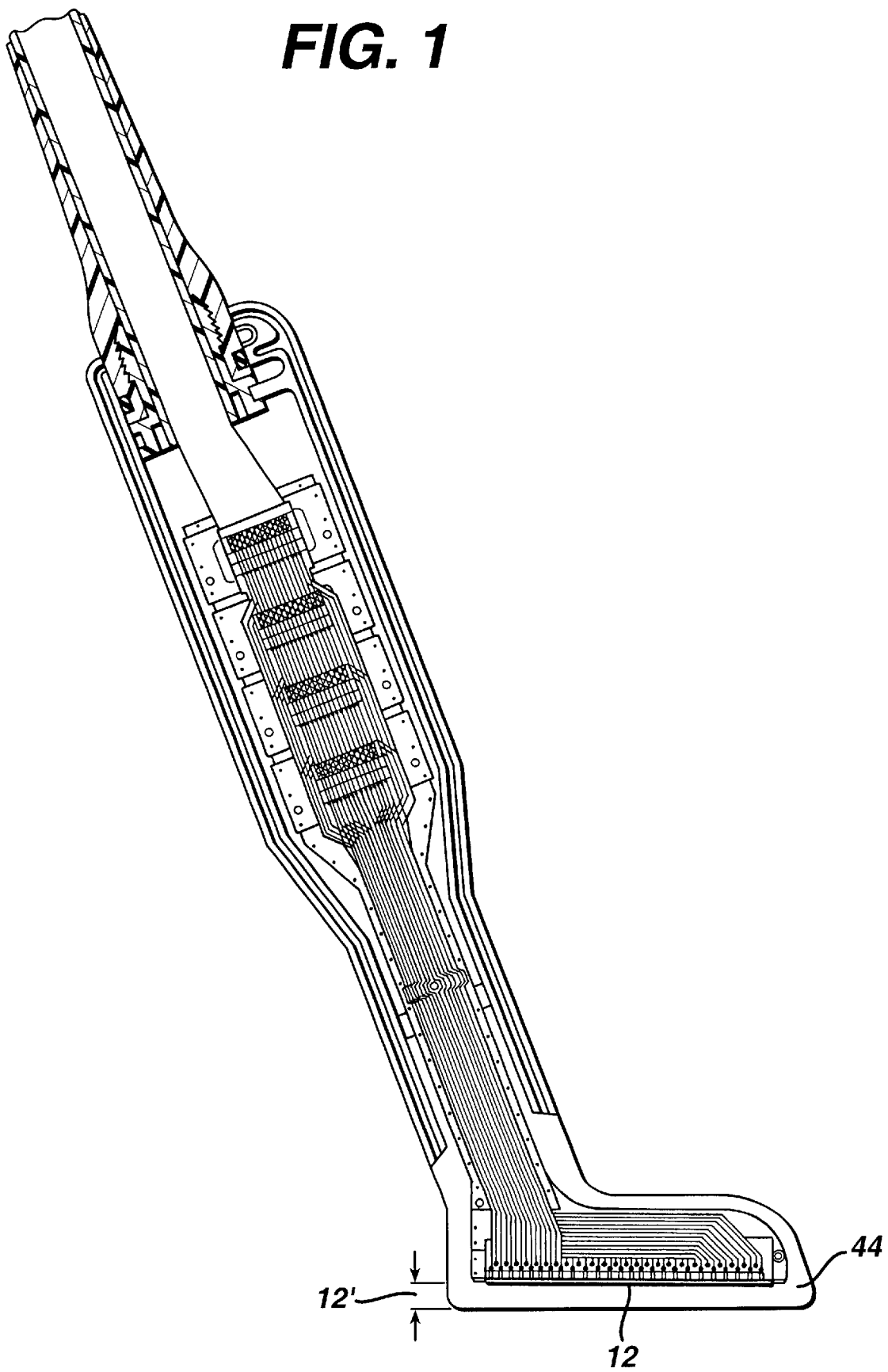
FIG. 1 shows an existing intraoperative ultrasound probe, which may be improved upon in accordance with the principles of the present invention.

Referring first to FIG. 1, the intraoperative ultrasound probe described in U.S. Pat. No. 5,381,795 is shown. Transducer 12 is shown encapsulated by RTV rubber 44, which creates an insulated boot and standoff around the transducer section as described in greater detail in the referenced patent. For the reasons described above, the use of standoff material with chemical and mechanical properties that enable the probe to be easily sterilized and disinfected and provide protection against electrical shock, also limits the maximum thickness 12' of the standoff due to its sub-optimal acoustic properties.

Figure 2:
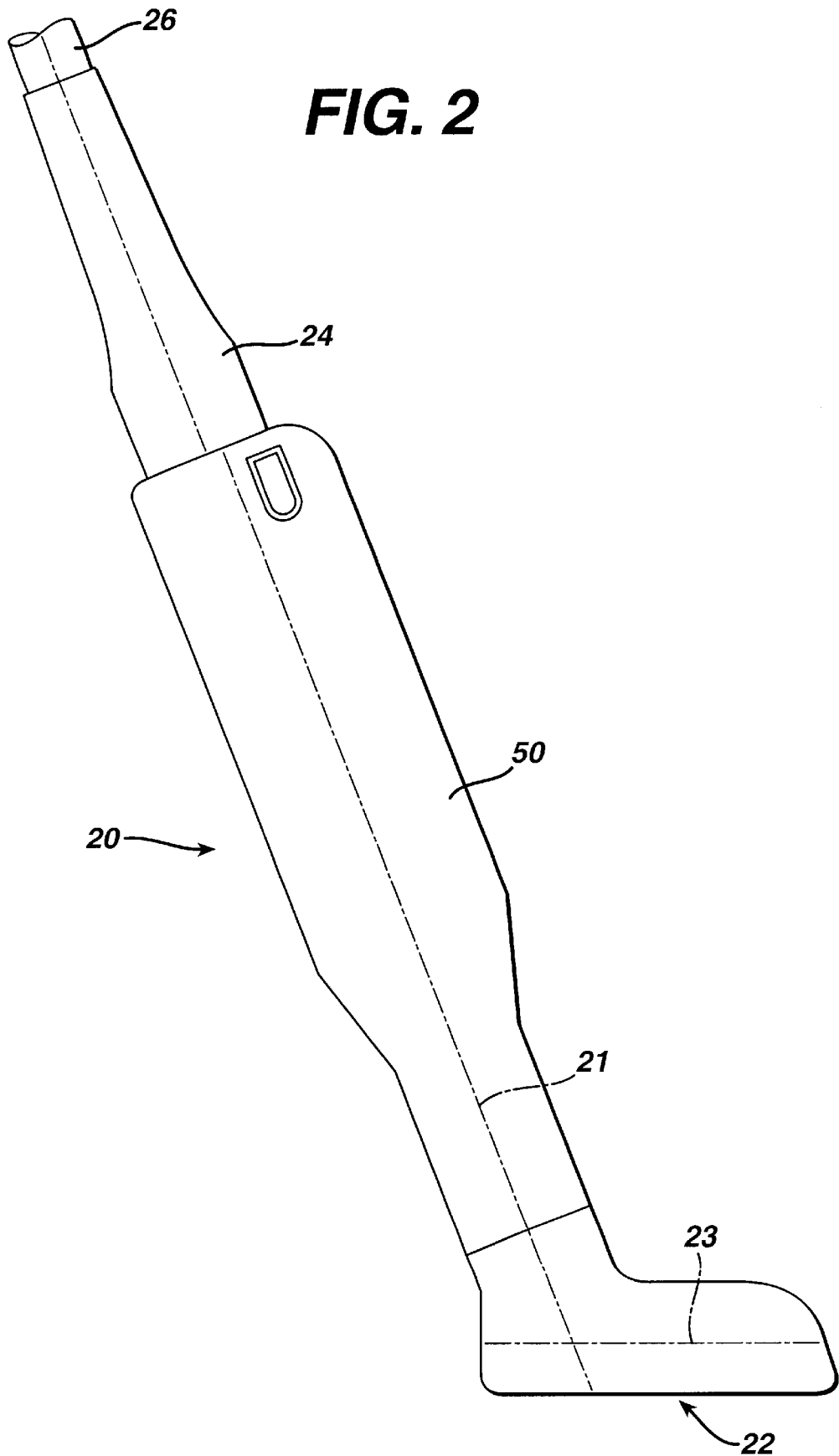
FIG. 2 shows the outline of an intraoperative ultrasound probe of the present invention.
Figure 3:
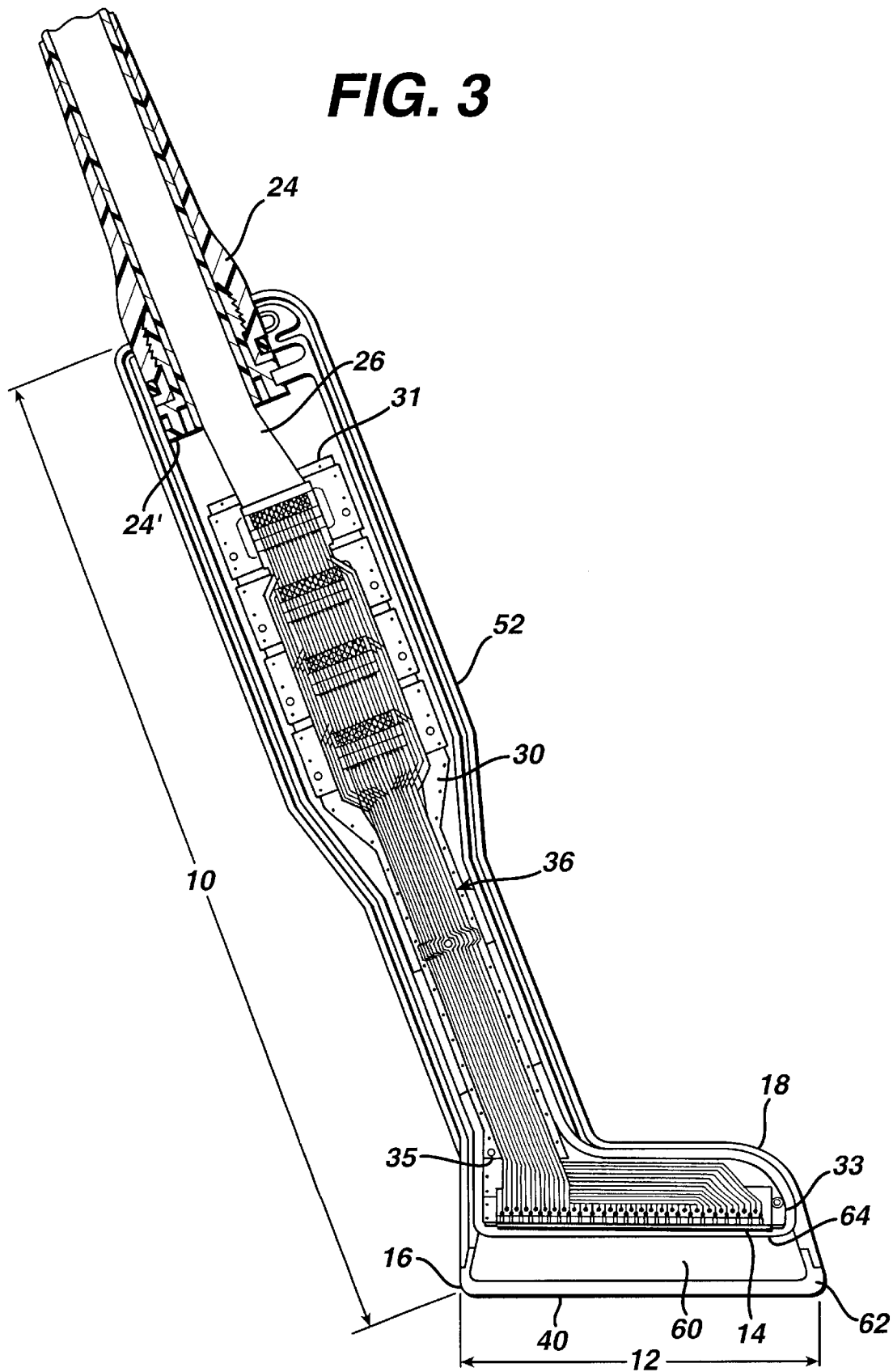
FIG. 3 shows a side section view of the intraoperative ultrasound probe of FIG. 2.
Figure 3A:
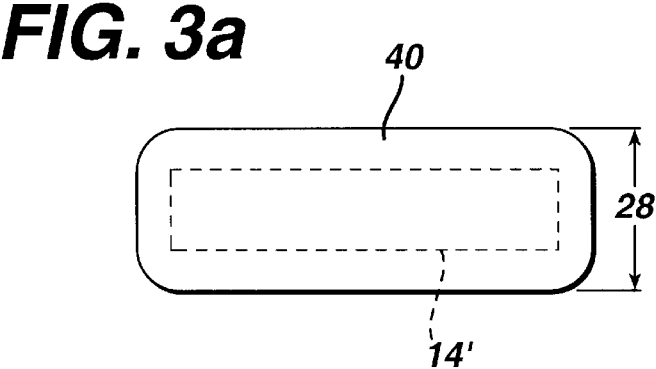
FIGS. 3a–3c show various bottom, end and cross sectional views of the intraoperative ultrasound probe the intraoperative ultrasound probe of FIG. 2.
Figure 3B:
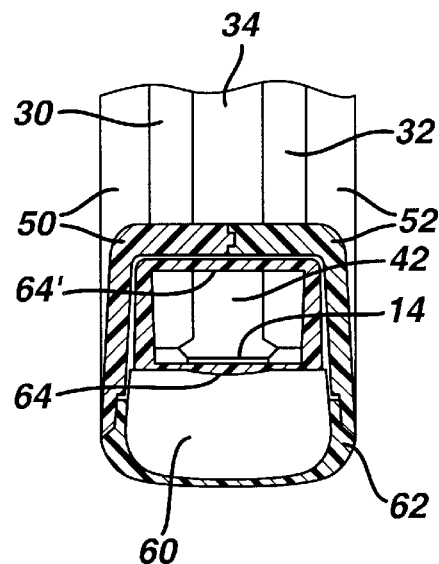
Figure 3C:
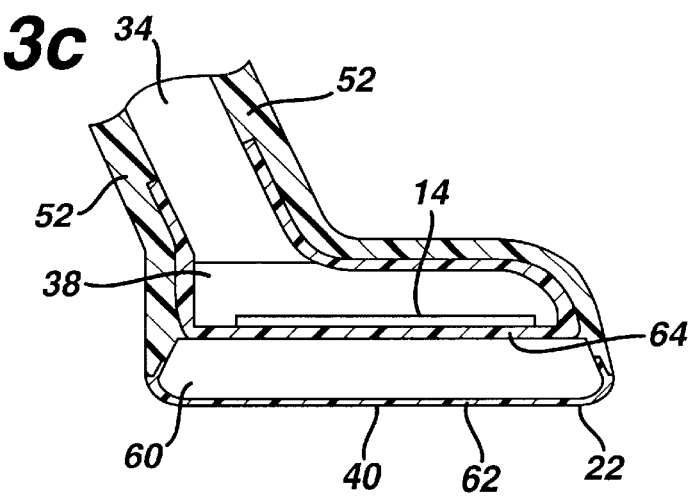

Turning now to FIGS. 2 and 3, the ultrasound probe of the present invention is shown, which makes improvements upon the ultrasound probe shown in FIG. 1. The ultrasound probe of the present invention is approximately L-shaped, resembling a tiny model of a leg or foot. The probe comprises a distal transducer section 22 resembling the "foot" (See also FIG. 3c) and a handle section 20 resembling the "leg," with a strain relief 24 and multifilament cable 26 exiting the proximal end of the handle section 20. Handle section 20 is comprised of case halves 50 and 52 that extend to cap 62 as shown in FIGS. 3, 3b and 3c. The cable 26 leads to a connector (not shown) suitable for connecting the probe to an ultrasonic diagnostic system, which drives the transducer of the probe and receives ultrasonic echo signals from the transducer in the conventional manner. U.S. Pat. No. 5,381,795 describes and illustrates a preferred termination assembly for connecting a multifilament coaxial cable and coaxial conductors to the intraoperative ultrasound probe of the present invention.

The major axis 23 of the transducer section 22 is inclined at an angle of 112 degrees with respect to the major axis 21 of the handle section. The length 10 of the handles section 20 from its proximal end to the heel 16 of the transducer section 22 is approximately 94 mm. The length 12 of the transducer section from heel 16 to its toe 18 is approximately 36.8 mm and the width 28 of the transducer section is approximately 12 mm as shown in FIG. 3a. In comparing the intraoperative ultrasound probe of the present invention with the intraoperative ultrasound probe of FIG. 1, it is noted that the transducer section 22 is shown having a greater thickness in the present invention for illustrative purposes only. An intraoperative ultrasound probe constructed in accordance with the principles of the present invention is similar in appearance and size to the probe shown in FIG. 1. The thickness of the transducer section of the present invention may vary for the reasons explained above but must not hinder the ease of use and manipulation of the probe by a user.

Referring now to FIGS. 3, 3b and 3c two matched printed circuit boards 30 and 32, each board having the inclined L-shape of the probe, are shown located inside case halves 50, 52 and the molded rubber boot that forms lens 64. Each printed circuit board extends from a top end 31 to a bottom distal end 33. The printed circuit boards are mounted in parallel, separated as shown in FIG. 3b by a spacer 34, extending from the top 31 of the printed circuit boards to a lower terminating edge 35. Each printed circuit board contains a plurality of conductive traces 36, which make electrical connections between the transducer crystal 14 and the upper surfaces of the boards as described and illustrated in U.S. Pat. No. 5,381,795.

Transducer crystal 14 is mounted perpendicular to the lower edges of the printed circuit boards 30 and 32. The transducer 14 has an overall length of approximately 28 mm and a width of approximately 4.2 mm. The transducer 14 is diced into an array of 128 finely pitched elements for the performance of B-scan and color flow Doppler imaging. The finely pitched elements transmit and receive over an operating frequency range of 7–15 MHz, giving the transducer the ability to visualize and diagnose a vessel that is immediately in contact with the footprint 40 of the probe. The footprint of the probe is shown in the bottom view of FIG. 3a, with the outline 14' of the transducer crystal indicated by a dashed line box.

In FIGS. 3b and 3c, side and front cutaway views of transducer section 22 are shown. Lens 64, standoff 60 and cap 62 are shown located below transducer 14. Transducer 14 is shown connected to circuit boards 30 and 32. The volume 42 above the transducer 14 and below the top inside edge 64' of lens 64, and between the printed circuit boards 30 and 32, is filled with a loaded epoxy backing material 38. The backing material attenuates acoustic waves emanating from the rear of the crystal.

Transducer 14 and backing material 38 are shown encased in an RTV rubber compound that extends to a point above terminating edge 35 (See FIG. 3). The RTV rubber compound creates a boot around transducer 14 and backing material 38. In a preferred embodiment of the present invention, the boot is formed by a molding process, which also forms lens 64. Lens 64 fully insulates the patient from the electrical connections to the transducer 14 and provides known transducer focusing properties.

Once lens 64 is formed, standoff 60 is adhered or bonded to lens 64 and then the cap 62 is adhered or bonded to the standoff. In a preferred embodiment of the present invention standoff 60 is a rubber material that has a longitudinal velocity between 1.4 to 1.6 mm/psec, an impedance between 1.4 MRayls and 1.60 MRayls, and an attenuation no greater than 0.10 dB/mm/MHz and cap 62 is constructed from a biocompatible elastomer having high chemical and mechanical resistance and acceptable acoustic characteristics. Standoff 60 extends approximately 5.2 mm below transducer 14. Cap 62 is approximately 0.38 mm in thickness. If desired, the volume filled by the standoff 60 can be sealed with a liquid tight gasket to allow the use of a liquid standoff material. The handle section 20 comprises two hollow clamshell case halves 50 and 52 formed of a rigid polysulfone plastic that cover transducer section 22 and extend to and are adhered to cap 62, which forms a sealed surface as shown in FIGS. 3, 3*b* and 3*c*.

The combination and placement of lens 64, standoff 60, cap 62 and case halves 50 and 52 provide a probe with an integrated standoff having optimal acoustic properties with no regard for the chemical or mechanical properties of the standoff. Such a standoff may be increased in thickness, as desired, to help place the focal zone at the area desired for the probe. In addition, cap 62 and case halves 50 and 52 form a sealed surface through adhesion or bonding that renders the probe easy to clean, disinfect and sterilize between uses, further enhancing patient safety and medical efficiency.

Figure 4A:
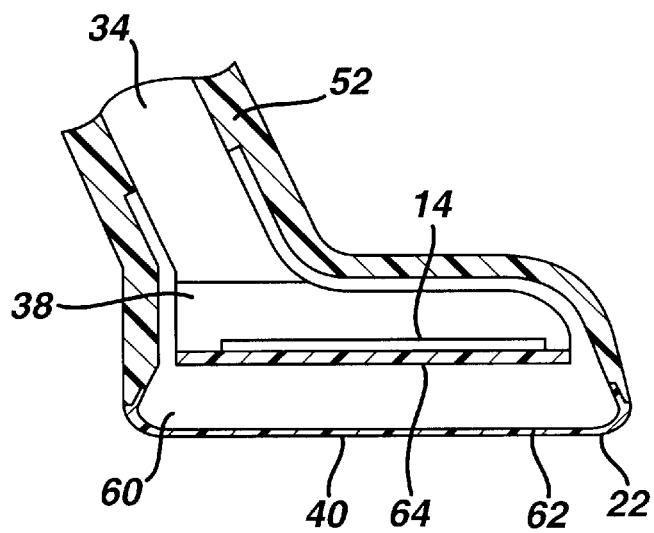
FIGS. 4a and 4b show alternative embodiments of an intraoperative ultrasound probe of the present invention.

Turning now to FIG. 4*a* a side cutaway view of transducer section 22 is shown in another embodiment of the present invention. Lens 64, standoff 60 and cap 62 are shown located below transducer 14. An RTV rubber compound is placed under transducer 14 to form lens 64. Lens 64, transducer 14 and backing material 38 are then encased in standoff 60. The standoff 60 forms a sealed boot around transducer 14, lens 64 and backing material 38. Standoff 60 insulates the patient from the electrical connections to the transducer. Such an arrangement provides an intraoperative ultrasound probe embodiment having the benefits of the present invention described above.

Figure 4B:
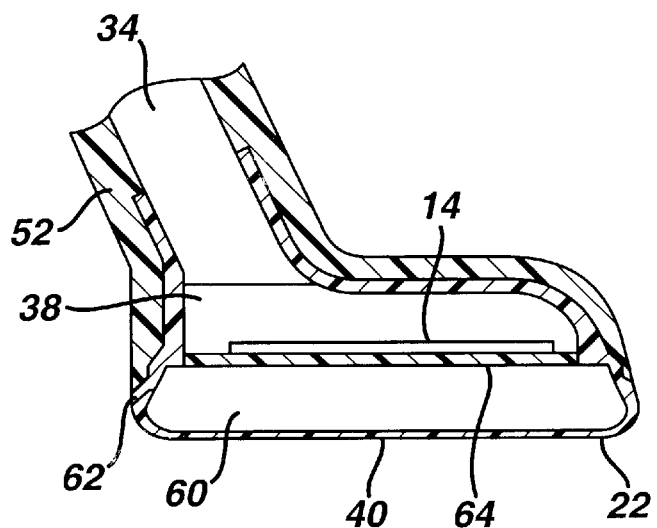

Turning now to FIG. 4*b* side cutaway view of transducer section 22 is shown in yet another embodiment of the present invention. Lens 64, standoff 60 and cap 62 are shown located below transducer 14. An RTV rubber compound is placed under transducer 14 to form lens 64. Lens 64 and transducer 14 and backing material 38 are then encased in cap 62. Cap 62 creates a sealed boot around transducer 14, lens 64 and backing material 38. Cap 62 insulates the patient from the electrical connections to the transducer. Such an arrangement provides another intraoperative ultrasound probe embodiment having the benefits of the present invention described above.

What is claimed is:

1. An intraoperative ultrasonic transducer probe comprising:

a patient-contacting surface for coming into contact with patients being examined by said probe, wherein said patient-contacting surface has an inner surface and an outer surface for patient contact; and a patient-contacting section containing a multielement ultrasonic transducer opposing said inner surface of said patient-contacting surface, said patient-contacting section having a longitudinal axis aligned with the longitudinal axis of said ultrasonic transducer; and a housing coupled to said patient contacting surface for sealing internal components of said probe; and a lens for focusing ultrasonic energy transmitted from said transducer; and a standoff for producing a spatial offset between said transducer and said patient-contacting surface;

wherein said standoff is spatially positioned between said lens and said inner surface of said patient-contacting surface.

2. The intraoperative ultrasonic probe of claim 1, wherein said standoff is a rubber material.

3. The intraoperative ultrasonic probe of claim 2, wherein said rubber material has a longitudinal velocity between 1.4 to 1.6 mm/psec, an impedance between 1.4 MRayls and 1.60 MRayls, and an attenuation no greater than 0.10 dB/mm/MHz.

4. The intraoperative ultrasonic probe of claim 3, wherein said standoff encloses said transducer.

5. The intraoperative ultrasonic probe of claim 1, wherein said standoff is a liquid.

6. The intraoperative ultrasonic probe of claim 1, wherein said lens material encloses said transducer.

7. The intraoperative ultrasonic probe of claim 6, wherein said lens electrically insulates said patient contacting section from said transducer.

8. The intraoperative ultrasonic probe of claim 7, wherein said lens is an RTV rubber compound.

9. The intraoperative ultrasonic probe of claim 1, wherein said patient-contacting surface is an elastomer.

10. The intraoperative ultrasonic probe of claim 9, wherein said patient-contacting surface encloses said transducer.

11. The intraoperative ultrasonic probe of claim 1, wherein said housing and said outer surface of said patient-contacting surface comprise means for cleaning, sterilizing and disinfecting said probe.

12. The intraoperative ultrasonic probe of claim 1, wherein said housing provides means suitable for being held by a person during use of the probe.

13. The intraoperative ultrasonic probe of claim 1, wherein said lens and said standoff and said patient contacting surface provide means for focusing said ultrasonic energy in the area in immediate contact with said outer surface.

14. An intraoperative ultrasonic transducer probe comprising:

a patient-contacting section containing a multielement ultrasonic transducer opposing a patient-contacting surface of the probe, said patient-contacting section having a longitudinal axis aligned with the longitudinal axis of said ultrasonic transducer; and a handle section suitable for being held by a physician during use of the probe, said handle section having a longitudinal axis and including means for connecting said probe to an ultrasonic diagnostic system, said handle section being attached to said patient-contacting section at one end of said handle section and at a point on said patient-contacting section which is offset from the center of said patient-contacting section, wherein the angle between said longitudinal axis of said patient-contacting section and said longitudinal axis of said handle section is an obtuse angle; and a standoff spatially located between said multielement ultrasonic transducer and said patient-contacting surface of the probe, and comprising means for producing a spatial offset between the surface of said multielement transducer and the patient-contacting surface of said probe for focusing said multielement transducer at the surface in immediate contact with said patient-contacting surface.

15. The intraoperative ultrasonic probe of claim 14, wherein said standoff further comprises a liquid tight, sterilizable encapsulation of said multielement transducer.

16. The intraoperative ultrasonic probe of claim 15, wherein said standoff is rubber.

17. The intraoperative ultrasonic probe of claim 16, wherein said is rubber has a longitudinal velocity between 1.4 to 1.6 mm/psec, an impedance between 1.4 MRayls and 1.60 MRayls, and an attenuation no greater than 0.10 dB/mm/MHz.

18. The intraoperative ultrasonic probe of claim 9, wherein said elastomer is biocompatible.

* * * * *

UNITED STATES PATENT AND TRADEMARK OFFICE
CERTIFICATE OF CORRECTION

PATENT NO. : 6,599,249 B1
DATED : July 29, 2003
INVENTOR(S) : Nordgren et al.

It is certified that error appears in the above-identified patent and that said Letters Patent is hereby corrected as shown below:

Column 2,
Line 25, "psec," should read -- $\mu$sec --.

Column 5,
Line 17, "psec," should read -- $\mu$sec --.

Column 6,
Line 24, "psec," should read -- $\mu$sec --.

Column 8,
Line 7, "psec," should read -- $\mu$sec --.

Signed and Sealed this

Thirteenth Day of July, 2004

JON W. DUDAS
*Acting Director of the United States Patent and Trademark Office*